US012711579B2

(12) United States Patent
Karami et al.

(10) Patent No.: US 12,711,579 B2
(45) Date of Patent: Aug. 18, 2026

(54) SENSOR FUSION

(71) Applicant: BASF Agro Trademarks GmbH, Ludwigshafen am Rhein (DE)

(72) Inventors: Mojtaba Karami, Cologne (DE); Nicolas Werner, Cologne (DE); Tim Toebrock, Cologne (DE); Ole Janssen, Cologne (DE); Christian Kerkhoff, Cologne (DE)

(73) Assignee: BASF Agro Trademarks GmbH, Ludwigshafen am Rhein (DE)

( * ) Notice: Subject to any disclaimer, the term of this patent is extended or adjusted under 35 U.S.C. 154(b) by 474 days.

(21) Appl. No.: 17/621,885

(22) PCT Filed: Jun. 26, 2020

(86) PCT No.: PCT/EP2020/068088
§ 371 (c)(1),
(2) Date: Dec. 22, 2021

(87) PCT Pub. No.: WO2020/260626
PCT Pub. Date: Dec. 30, 2020

(65) Prior Publication Data

US 2022/0253991 A1 Aug. 11, 2022

(30) Foreign Application Priority Data

Jun. 28, 2019 (EP) .................................... 19183266
Jun. 28, 2019 (EP) .................................... 19183430

(51) Int. Cl.
*G06T 5/20* (2006.01)
*G01N 21/3563* (2014.01)
(Continued)

(52) U.S. Cl.
CPC ........... *G06T 5/20* (2013.01); *G01N 21/3563* (2013.01); *G01N 33/0098* (2013.01);
(Continued)

(58) Field of Classification Search
CPC ............ G06T 5/20; G06T 2207/30188; G01N 21/3563; G01N 33/0098; A01B 79/005;
(Continued)

(56) References Cited

U.S. PATENT DOCUMENTS

2008/0063270 A1* 3/2008 McClelland .............. G06T 7/73
342/357.34
2008/0234935 A1* 9/2008 Wolf ...................... G01C 19/02
701/472
(Continued)

FOREIGN PATENT DOCUMENTS

EP 3219184 9/2017
EP 3299996 3/2018
(Continued)

OTHER PUBLICATIONS

Portz, G., Molin, J.P. & Jasper, J. Active crop sensor to detect variability of nitrogen supply and biomass on sugarcane fields. Precision Agric 13, 33-44 (2012). https://doi.org/10.1007/s11119-011-9243-4 (Year: 2012).*
(Continued)

*Primary Examiner* — Arleen M Vazquez
*Assistant Examiner* — Denise R Karavias
(74) *Attorney, Agent, or Firm* — ArentFox Schiff LLP

(57) ABSTRACT

A method for correcting remote sensor data of an agricultural field, comprising: receiving remote sensor data (DR) for the agricultural field from a remote sensor, wherein the remote sensor data (DR) comprises at least one remote measurement value corresponding to at least one location; receiving local sensor data (DL) for the agricultural field from at least one local sensor, wherein the at least one local sensor data (DL) comprises at least one local measurement value corresponding to at least one location of the at least one local sensor and corresponding to at least one point in
(Continued)

Figure 1:
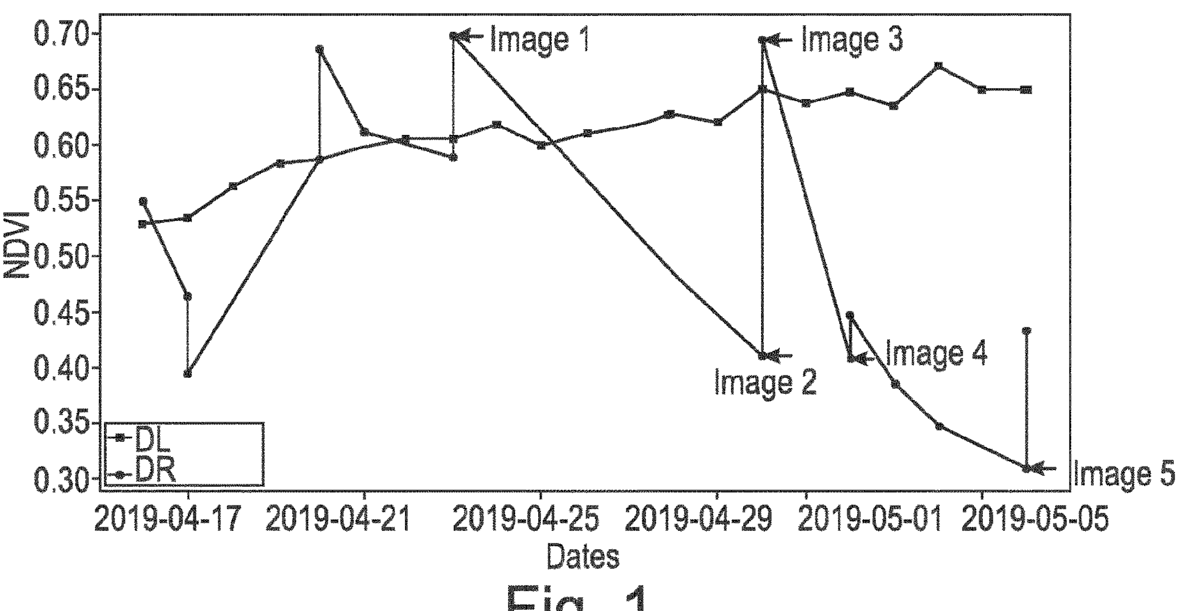

time of obtaining the local measurement value correlating to the remote measurement value; determining a correction model based on the previously received local sensor data (DL) and the remote sensor data (DR); and determining corrected current remote sensor data (DRP, DRPR) by applying the correction model to current remote sensor data.

15 Claims, 5 Drawing Sheets

(51) Int. Cl.
*G01N 33/00* (2006.01)
*A01B 79/00* (2006.01)
*A01M 7/00* (2006.01)

(52) U.S. Cl.
CPC .......... *A01B 79/005* (2013.01); *A01M 7/0089* (2013.01); *G06T 2207/30188* (2013.01)

(58) Field of Classification Search
CPC ... A01B 69/008; A01M 7/0089; G01D 21/02; G06N 3/044; G06N 3/08; G06F 18/25
See application file for complete search history.

(56) References Cited

U.S. PATENT DOCUMENTS

2009/0150000 A1 6/2009 Stelford et al.
2009/0265098 A1* 10/2009 Dix .................... G05D 1/0278 701/23
2012/0101634 A1 4/2012 Lindores
2013/0191017 A1* 7/2013 Peake ................. G05D 1/0227 701/410
2013/0274635 A1* 10/2013 Coza ..................... G16H 40/63 600/595
2015/0278640 A1* 10/2015 Johnson .............. G06V 20/188 382/110
2016/0003790 A1* 1/2016 Osborne ................. A01G 7/00 702/189
2018/0070527 A1 3/2018 Richt
2018/0302741 A1* 10/2018 Ikemoto ................. G06F 13/00
2019/0050948 A1 2/2019 Perry et al.
2019/0130547 A1* 5/2019 Pacifici .................... G06T 5/73

FOREIGN PATENT DOCUMENTS

WO 2016/076289 A1 5/2016
WO 2019/121097 6/2019

OTHER PUBLICATIONS

International Search Report and Written Opinion of International Application No. PCT/EP2020/068088 mailed Oct. 2, 2020, 11 pgs.
Huang et al., "Agricultural remote sensing big data: Management and applications", Journal of Integrative Agriculture, vol. 17, No. 9, 2018, pp. 1915-1931.
Prey et al., "Simulation of satellite reflectance data using high-frequency ground based hyperspectral canopy measurements for in-season estimation of grain yield and grain nitrogen status in winter wheat", ISPRS Journal of Photogrammetry and Remote Sensing, vol. 149, 2019, pp. 176-187.

* cited by examiner

SENSOR FUSION

CROSS-REFERENCE TO RELATED APPLICATION(S)

This application is a national stage entry under 35 U.S.C. § 371 of International Application No. PCT/EP2020/068088, filed on Jun. 26, 2020, which claims the benefit of priority of European Patent Application Nos. 19183430.8 and 19183266.6, both filed on Jun. 28, 2019, the disclosures of which are hereby incorporated by reference herein in their entireties.

TECHNICAL FIELD

The present disclosure relates to a method, a processing device, a system, a computer program, a computer program and a computer non-volatile storage medium for correcting remote sensor data of an agricultural field.

BACKGROUND

For precision farming the quality of plant, disease and pest models form the basis to translate data into actionable insights and automated operations on agricultural fields. The quality of such models is highly dependent on real world data. Two examples are satellite or weather data. Particularly, for satellite images limitations in availability and quality due to e.g. long revisit times, cloud or atmospheric effects exist.

Accuracy and performance of modern plant and pest models are highly dependent on several field-specific high-quality weather and crop data. Today's weather models already have a high precision, however some specific field weather parameter with a high impact on modeling needs further improvement and ground-truth to reduce modeling errors caused by input data. In particular, locations with field-specific microclimatic conditions benefit from additional in-situ measurements.

To further improve spray recommendations more elaborate techniques to enhance data quality are required. Additionally, data availability and reliability are pre-requisites in modern farming to safe operations on agricultural fields.

In regard of satellite image availability and quality, numerous market offers for satellite-based biomass and crop health analytics exist. However, those are all limited by image availability and quality. These issues are tried to be mitigated by increasing the number of ingested satellite products and incorporation of post-processing steps (e.g. atmospheric correction). However, these measures are affecting costs of those market offers.

Installation and maintenance of IoT devices or non-stationary sensors is time consuming. Existing offers usually require significant installation and high maintenance efforts. This impacts growers' resources, i.e. people can less focus on the agronomic learning rather than keeping the systems running and maintained.

In times of "Big Data" growers are very much concerned with collecting and governing data from their fields, however, this does not necessarily mean more insight and more efficient farming practice. Digital farming platforms often lack the ability that digests data and turn this into practical insights and recommendations.

Remote sensor data is often used to provide additional data of the agricultural field. Such remote sensors providing the remote sensor data for example are satellites, which are able to cover the entirety of an agricultural field. However, in particular to the distance of the remote sensor to the agricultural field, measurement errors might be introduced. For example, atmospheric distortions such as clouds might distort the remote sensor data.

Thus, there is a need for an improved method of obtaining remote sensor data of an agricultural field.

INVENTION

The following disclosure applies to the systems, methods, computer programs, computer readable non-volatile storage media, and computer program products disclosed herein alike. Therefore, no differentiation is made between systems, methods, computer programs, computer readable non-volatile storage media or computer program products. All features are disclosed in connection with the systems, methods, computer programs, computer readable non-volatile storage media, and computer program products disclosed herein.

According to one aspect of the invention, a method for correcting remote sensor data of an agricultural field is provided, the method comprises the following steps: receiving remote sensor data for the agricultural field from a remote sensor, wherein the remote sensor data comprises at least one remote measurement value corresponding to at least one location that is measured by the remote sensor at at least one point in time of obtaining the remote measurement value; receiving local sensor data for the agricultural field from at least one local sensor, wherein the at least one local sensor data comprises at least one local measurement value corresponding to at least one location of the at least one local sensor and corresponding to at least one point in time of obtaining the local measurement value correlating to the location and point in time of obtaining the remote measurement value; determining a correction model based on the previously received local sensor data and the previously received remote sensor data; and determining corrected current remote sensor data by applying the correction model to current remote sensor data.

The term "current remote sensor data", as used herein, relates to current remote sensor data, in particular satellite data, to which the correction model for determining corrected current remote sensor data is applied. In other words, the current remote sensor data e.g. relates to live remote sensor data, which are provided in real-time, e.g. by a satellite.

The terms "remote sensor data" and "local sensor data", as used herein, relate to any sensor data, including historic sensor data. In other words, the remote sensor data and the local sensor data describe the available sensor data used to determine the correction model. It should be noted that the remote sensor data and the local sensor data can be obtained shortly before obtaining current remote sensor data, or long before obtaining current remote sensor data.

The term "determining the correction model", as used herein, comprises training and learning of the correction model, in particular based on remote sensor data and local sensor data.

The term "corrected current remote sensor data", as used herein, relates to current remote sensor data, which have been corrected. Correcting the current remote sensor data comprises an amendment of the current remote sensor data or a validation of the current remote sensor data.

In other words, in a scenario, in which the previously received local sensor data indicate that the previously received remote sensor data are already sufficiently accurate, the correction model determines based on the previously received local sensor data and the previously received remote sensor data that the previously remote sensor data do not have to be amended. Consequently, the correction model determines that the corrected current remote sensor data are the previously received remote sensor data without amending the previously received remote sensor data. Thus, the correction model validates the previously received remote sensor data, or in other words the correction model confirms a sufficient accuraccy of the previously received remote sensor data.

In a scenario, in which the previously received local sensor data indicate that the previously received remote sensor data are not sufficiently accurate, the correction model determines based on the previously received local sensor data and the previously received remote sensor data that the previously remote sensor data have to be amended. Thus, the correction model amends the previously received remote sensor data. The correction model is provided with predetermined thresholds used for determining, if the previously received remote sensor data already is sufficiently accurate in view of the previously provided local sensor data.

In addition, the correction model is provided with a predetermined outlier threshold used for determining, if the previously received remote sensor data is an outlier. The outlier will not be corrected by the correction model but rather directly discarded.

The term "agricultural field", as used herein, comprises any kind of commercially used area, in particular forest area, meadows and farmland.

According to an embodiment, the remote sensor is disposed distant to the agricultural field, for example integrated in a satellite.

According to an embodiment, the local sensor is disposed near or in the agricultural field.

According to an embodiment, the method, as described herein, is a computer-implemented method.

According to an embodiment, the correction model determines corrected current remote sensor data based on the current remote sensor data and current local sensor data.

Based on local sensor data, or in-situ field data, correction or projection models may be determined leading to enhanced data quality or refined models. Both lead to more robust model performance in the former case due to enhanced model inputs and in the latter case due to refinement of the model itself. The latter case may be particularly relevant for weather models, growth stage models, pest or disease models plus any zone-specific elements reflected in such models. Such an approach provides benefits for the farmer in that the recommendations provided are tailored to the conditions present in a specific field and farmer's efforts to visit the field are reduced.

In one implementation, the local sensor, or on-site observation sensor, provides at least one measurement value relating to one or more condition(s) on an agricultural field. In one implementation the measurement value relates to weather, soil and/or crop conditions in the agricultural field. Examples of measured or derived weather conditions are air temperature, humidity, pressure, precipitation, wind, growing degree days. Crop conditions may be measured or derived through a spectrometer e.g. based on reflectance measurements to determine a biomass index, such as normalized difference vegetation index (N DVI), leaf area index (LAI) or photosynthetically active radiation (PAR), or leaf wetness. NDVI for instance is based on red and near infrared spectral reflectance measurements acquired in the red (visible) and near-infrared regions, respectively. These spectral reflectances are ratios of the reflected over the incoming radiation in each spectral band individually, hence they take on values between 0.0 and 1.0. Soil conditions may include reflectance or in soil measurements relating to nutrient content, soil composition and the like. More than one condition on the agricultural field may be measured simultaneously by including respective sensor elements into the local sensor. The remote sensor data may include one or a combination of conditions mapped on a grid as measurement value and hence be comparable to the in situ in field or local sensor data.

In one embodiment, the local sensor provides a multiple-band spectrometer, air temperature, humidity, pressure, PAR, GPS coordinates, acoustic sonogram (sound classification), tilt, compass and/or, acceleration. Examples of data that can be derived from local sensor are leaf temperature from upwelling longwave, flowering or pollination from spectrometer and photosynthesis (A) from PAR, fraction of available PAR, and Light Use Efficiency (LUE).

Here, the first point in time may be viewed as the closest matching point in time in both data sets, namely the remote sensor data and the local sensor data. The remote sensor data may include a time series of satellite images. The remote sensor data may be a multivariate time series including e.g. a two-dimensional grid of measurement values such as NDVI or LAI. The local sensor data may include a time series of measurement values each associated with the location of the local sensor. The local sensor data may be a univariate time series including e.g. a one-dimensional chain of measurement values such as NDVI or LAI. According to an embodiment the location of the local sensor corresponds to a positioning value as provided by a positioning system embedded into the local sensor. The positioning system e.g. comprises a global positioning system.

In one implementation, the local sensor may be non-stationary. Further the location of the local sensor may be a current or a corrected location. A corrected location may be determined according to the method for correcting local sensor data received from the local sensor, as described herein.

In one implementation, local sensor data from multiple local sensors in different locations of the field or multiple univariate time series are received. If more than one local sensor is placed in the agricultural field in different locations of the field intra-field variability is mapped, and localization dependencies may be considered for the correction model. In one implementation, local sensors placed near the field of interest e.g. neighboring fields or in a distance lower than a threshold away from the field of interest may be considered.

In one implementation, the correction model is determined for more than one point in time and/or location. If the correction model is determined for more than one point in time, local sensor data and remote sensor data are matched according to a common time stamp. In such a case the correction model becomes time-dependent and potential in season variations may be reflected. If the correction is determined for more than one location, intra field variability may by reflected. A combination of time and location results in a more accurate correction model reflecting both, intra field variability as well as seasonal variations.

In one implementation, the correction model may be determined and applied to remote sensor data confined to the agricultural field of interest. Additionally or alternatively the correction model may be determined for remote sensor data confined to a first agricultural field of interest and applied to remote sensor data relating to a second agricultural field of interest. In such a case the correction model's applicability to e.g. neighboring fields or field lying within a distance of the first field may be validated. Such validation may be determined empirically via a static or pre-defined distance threshold. Alternatively or additionally such validation may be determined dynamically by analyzing observations in the region of interest with more than one agricultural field. In this context, the agricultural field may be specified by the field boundary or the crop type cultivated on the agricultural field. Applying the correction model to other field allows for broader application and adds the benefit for farmers. If for instance only one field is equipped with local sensors, the determined correction function may also be used for neighboring fields not equipped with such sensors.

Consequently, the current remote sensor data provided by a remote sensor is systematically corrected based on a trained correction model.

Combining spectral, in-situ time series from local sensor with satellite imagery provides continuous, high-precision monitoring of field zone biomass, enabling precision zone spray solution that will be available every-day.

Thus, more consistent and more accurate remote sensor data is provided. Further, an improved method for correcting remote sensor data of an agricultural field is provided.

In an embodiment, the local sensor is non-stationary.

Thus, local sensor data or in-situ field data that is collected through a local sensor placed on or near to an agricultural field of interest in larger gridded data sets from remote sensing is provided. The local sensor may be non-stationary. According to an embodiment, the local sensor is non-stationary in the sense that it is movable in the agricultural field by being placed in intermittent locations. Hence, for a first time period the local sensor may be placed in a first location of the field and for a second time period the local sensor may be placed in a second location of the field. For example, a farmer repositions the local sensor, when the local sensor disturbs the farming in his work. In other words, the farmer might reposition the local sensor in a range of a couple of meters. In both cases, the local sensor collects time series data, which may be available on a certain time scale e.g. seconds, minutes, days, weeks, month or years. In or in close proximity to the field multiple local sensors may be placed. However, the local sensors do not cover the entirety of the agricultural field at every time.

Thus, an improved method for correcting remote sensor data of an agricultural field is provided.

In an embodiment, the remote measurement value and/or the local measurement value is associated with a hyperspectral index or a biomass index.

In one implementation, the remote measurement value and e.g. the local measurement value may be associated with or may be a hyperspectral or a biomass index such as NDVI. In such a case the local sensor is e.g. equipped with a spectrometer, e.g. a multi-band spectrometer measuring at least in the red to infrared region. Additionally, the sensor may be positioned above and/or below the canopy. Above and below position allows to determine absolute biomass indices like LAI. In case of a non-stationary sensor, it may be placed on e.g. a pole or a post elevating the position of the sensor above the ground.

Thus, an improved method for correcting remote sensor data of an agricultural field is provided.

In an exemplary embodiment, determining the correction model comprises the following steps: determining the remote measurement value corresponding to the location of the at least one local sensor; determining a difference between the remote measurement value corresponding to the location of the at least one local sensor and the local measurement value of the at least one local sensor for a plurality of points in time, wherein determining the correction model is further based on the determined difference.

According to an embodiment, the correction model determines an average difference between the remote measurement value and the local measurement value for a specific location in the agricultural field for a plurality of points in time. The correction model then determines a corrected remote measurement value, and thus corrected remote sensor data, for each point in time based on the determined average difference.

Thus, a correction model is determined, that corrects the remote sensor data more consistently and more accurately.

Thus, an improved method for correcting remote sensor data of an agricultural field is provided.

In an embodiment, the remote sensor data comprises at least one remote image, which is based on the at least one remote measurement value, wherein determining the remote measurement value corresponding to the location of the local sensor comprises the following step: extracting a pixel from the remote image that is closest to the location of the local sensor or extracting a mean of pixels within a predefined distance of the pixel closest to the location of the local sensor; determining the remote measurement value based on the extracted pixel, wherein determining the correction model is also based on the extracted pixel on which the remote measurement value bases. The remote sensor data comprises at least one remote image, which is based on the at least one remote measurement value of the remote sensor data. The remote image preferably is a satellite image. Each pixel of the remote image relates to a remote measurement value.

In other words, the remote measurement value from remote sensor data associated with the location e.g. the current or corrected location, is determined by extracting a pixel from the remote sensor data that is closest to the location e.g. the current or corrected location or by extracting a mean of pixels within a predefined distance of the pixel closest to the location e.g. the current or corrected location. For remote sensor data based on reflectance for instance multiple optical bands may be included. Based on the spectral response function of the remote sensor data and the local sensor data the measurement values from each data set may be matched, if the comparison is done on a band level. For relative measurement values, this may not be required.

Consequently, more consistent and accurate remote sensor data is provided.

Thus, an improved method for correcting remote sensor data of an agricultural field is provided.

In an embodiment, determining a difference between the remote measurement value comprises the following steps: receiving local time series data of the local sensor data from the at least one local sensor, wherein the local time series data comprises a plurality of location data of a plurality of points in time corresponding to the location, where the at least one local sensor is located at a specific point in time; determining a cluster of local sensor data based on a maximal distance between the respective locations of the local sensors over time; determining a clustered location of the at least one local sensor based on the determined cluster; determining the difference between the remote measurement value corresponding to the clustered location of the at least one local sensor and the local measurement value of the at least one local sensor for a plurality of points in time, wherein determining the correction model is further based on the determined difference.

Once the clusters are determined, a new sensor data point may be checked, if it lies within one of the clusters. If a cluster is identified, the corresponding corrected location associated with the measurement value of the new sensor data point may be stored. If no cluster is identified, this may be flagged as device movement and/or the method for correcting local sensor data may be repeated to determine respective cluster center.

By correcting the location of each local sensor data point, inaccuracies in the positioning system of the local sensor can be avoided and the overall data quality for sensor fusion improved. In particular for movable local sensors, such inaccuracies have high impact on the further processing of the data and can induce additional errors. The method thus allows matching the trajectory of local sensor measurements with large-scale pixel or gridded data sets and accounting for random fluctuations in positioning system. Detecting physical device movements (signal/noise) is crucial in combining data from movable local sensors (e.g. a NDVI time series) with other sources (e.g. NDVI time series from satellites). In essence the detection of physical sensor movements is done through machine learning (e.g. hierarchical clustering), and filtering of satellite GPS signals.

In one implementation the clusters are determined based on at least one of the cluster analysis methods hierarchical clustering, particularly single-linkage hierarchical clustering, centroid-based clustering, distribution-based clustering or density-based clustering.

In one implementation, the determination of clusters is based on a distance between locations optionally including a pre-defined maximum distance to separate between clusters.

Thus, an improved method for correcting remote sensor data of an agricultural field is provided.

In an embodiment, the clustered location is determined by determining a center of the cluster.

In one implementation, the determination of cluster centers may be based on a distribution function. Here a simple radial distance or a maximum of the distribution function may be defined as cluster center.

Thus, an improved method for correcting remote sensor data of an agricultural field is provided.

In an embodiment, the method comprises the following steps: if the received remote time series data comprises at least one gap, where remote sensor data at an expected point in time in the time series of remote time series data are missing, then receiving local sensor data for the point in time of the gap and determining predicted remote sensor data for the point in time of the gap based on the received local sensor data.

According to an embodiment, the correction model predicts the remote sensor data, in particular using a statistical model that is fed with the local sensor data and/or the remote sensor data.

Remote sensor data can be highly irregular and hence certain point in times are missing in such measurement. Generating remote sensor data for such missing point in times allows to provide the farmer with more current information on the field status, more accurate modelling in such gaps and hence more accurate recommendations or decisions. In this context gaps include missing remote sensor data between two points, where remote sensor data is available, or missing remote sensor data following one point, where remote sensor data is available. Hence the method allows projecting current remote sensor data into the future until the next set of remote sensor data is received. Thus, the method allows to increase data availability and to provide the farmer with a current, up-to-date view on the field despite the irregularity of remote sensor data.

Thus, even large gaps can be filled out with predicted remote sensor data. Further, more frequent images from remote sensors can be provided even if not current remote sensor data is available.

Thus, an improved method for correcting remote sensor data of an agricultural field is provided.

In an embodiment, determining the predicted remote sensor data comprises: Receiving remote sensor data of a point in time just before the gap and determining the predicted remote sensor data based on the received remote sensor data of the point in time just before the gap.

Thus, a simple solution is provided for estimating the predicted remote sensor data. Further, an improved method for correcting remote sensor data of an agricultural field is provided.

In an embodiment, the correction model comprises a projection function depending on historical data sets of remote sensor data and local sensor data, wherein the predicted remote sensor data is determined based on the projection function.

In other words, the projection function is determined for a time series of local sensor data up to the gap. A time dependent projection function may be generated taking account of e.g. seasonal variations. Here time series modelling techniques such as autoregression, Bayesian techniques or more sophisticated recurrent neural networks such as long short-term memory (LSTM), echo state network (ESN), ordinary differential equations (ODE) or stochastic partial differential equations (SPDE). Additionally, gaussian process regression techniques may be used to take account of the irregular or discontinuous nature of remote sensor data.

Thus, an improved method for correcting remote sensor data of an agricultural field is provided.

According to another aspect of the invention, a processing device is configured for receiving remote sensor data for the agricultural field from a remote sensor, wherein the remote sensor data comprises at least one remote measurement value corresponding to at least one location that is measured by the remote sensor at at least one point in time of obtaining the remote measurement value; receiving local sensor data for the agricultural field from at least one local sensor, wherein the at least one local sensor data comprises at least one local measurement value corresponding to at least one location of the at least one local sensor and corresponding to at least one point in time of obtaining the local measurement value correlating to the location and point of time of obtaining the remote measurement value, determining a correction model based on the previously received local sensor data and the previously received remote sensor data; determining corrected current remote sensor data by applying the correction model to current remote sensor data.

Thus, an improved method for correcting remote sensor data of an agricultural field is provided.

According to another aspect of the invention, a system for correcting remote sensor data of an agricultural field comprises a remote sensor, configured for providing remote sensor data for the agricultural field from a remote sensor, wherein the remote sensor data comprises at least one remote measurement value corresponding to at least one location that is measured by the remote sensor at at least one point in time of obtaining the remote measurement value; a local sensor, configured for providing local sensor data for the agricultural field from at least one local sensor; wherein the at least one local sensor data comprises at least one local measurement value corresponding to at least one location of the at least one local sensor and corresponding to at least one point in time of obtaining the local measurement value correlating to the location and point of time of obtaining the remote measurement value; and a processing device, as described herein.

According to another aspect of the invention, a computer program is provided comprising computer readable instructions, which when loaded and executed by a processing device perform the methods, as described herein.

According to another aspect of the invention, a computer readable non-volatile storage medium is configured for storing a computer program, as described herein.

According to another aspect of the invention, a use of remote sensor data for the agricultural field and local sensor data for the agricultural field in a method, as described herein, is provided.

In one implementation, a method for correcting remote sensing data of an agricultural field of interest based on local sensor data from on-site observation sensor is provided, the method comprising the following steps: receiving, via a communication interface, local sensor data for the agricultural field of interest, wherein the local sensor data includes at least one first time point, at least one measurement value and a location of the observation sensor; receiving, via a communication interface, remote sensor data for the agricultural field of interest including the same or a derived measurement value in relation to the local sensor data for the at least one first time point; determining, via a processing unit, a correction model based on the measurement value from remote sensing data associated with the current or corrected location of the local sensor data and based on the measurement value of the local sensor data; applying, via the communication interface, the correction model to the remote sensing data and provide corrected remote sensing data.

In one implementation, the observation sensor is non-stationary or stationary.

In one implementation, the location of the observation sensor is a current or a corrected location.

In one implementation, the measurement value is associated with a hyperspectral or a biomass index.

In one implementation, the measurement value from remote sensing data associated with the location is determined by extracting a pixel from the remote sensing data that is closest to the location or by extracting a mean of pixels within a predefined distance of the pixel closest to the location.

In one implementation, wherein the correction model is determined for more than one time point and/or location.

In one implementation, a method for correcting local sensor data received from an on-site observation sensor, in particular from a locally non-stationary sensor, further in particular movable with intermittent location is provided, the method comprising the following steps: receiving, via a communication interface, time series data from the on-site observation sensor, wherein the time series data includes for each time point at least one measurement value associated with a location; determining, via the processing unit, one or more clusters in the time series data based on the location; determining, via a processing unit, for each determined cluster a cluster center; providing, via the communication interface, the determined cluster center as corrected location associate with each measurement value in each cluster.

In one implementation, on receipt of a new sensor data point, the new sensor data point is checked, if it lies within one of the determined clusters. If the new sensor data point does not lie within one of the determined clusters, it is assumed that a local sensor has been significantly repositioned. Consequently, a new cluster is determined, and a determination of a corresponding cluster center is repeated.

In one implementation, a method for filling gap(s) in a time series of remote sensing data based on local sensor data is provided, the method including the following steps: receiving, via a communication interface, a time series of remote sensing data from a database with gaps, for which no remote sensing data exists; receiving, via a communication interface, local sensor data for at least time point lying in the gap; determining, via a processing unit, remote sensing data for time points in the gap based on remote sensing data just before the gap and received local sensor data during the gap using a projection function, wherein the projection function is parametrized according to historical data sets of remote sensing data and local sensor data; providing, via the communication interface, projected remote sensing data at the identified point in time, where no remote sensing data exists.

In one implementation, a system for correcting remote sensing data of an agricultural field of interest based on local sensor data from on-site observation sensor is provided, the system comprising a communication interface and a processing unit configured to: receiving, via a communication interface, local sensor data for the agricultural field of interest, wherein the local sensor data includes at least one first time point, at least one measurement value and a location of the observation sensor; receiving, via a communication interface, remote sensor data for the agricultural field of interest including the same or a derived measurement value in relation to the local sensor data for the at least one first time point; determining, via a processing unit, a correction model based on the measurement value from remote sensing data associated with the current or corrected location of the local sensor data and based on the measurement value of the local sensor data; applying, via the communication interface, the correction model to the remote sensing data and provide corrected remote sensing data.

In one implementation, a system for correcting local sensor data received from an on-site observation sensor, in particular a locally non-stationary sensor, further in particular movable with intermittent location, is provided, the system comprising a communication interface and a processing unit configured to: receiving, via a communication interface, time series data from the on-site observation sensor, wherein the time series data includes for each time point at least one measurement value associated with a location; determining, via the processing unit, one or more clusters in the time series data based on the location; determining, via a processing unit, for each determined cluster a cluster center; providing, via the communication interface, the determined cluster center as corrected location associate with each measurement value in each cluster.

In one implementation, a system for filling gap(s) in a time series of remote sensing data based on local sensor data, is provided, the system comprising a communication interface and a processing unit configured to: receiving, via a communication interface, a time series of remote sensing data from a database with gaps, for which no remote sensing data exists; receiving, via a communication interface, local sensor data for at least one time point lying in the gap; determining, via a processing unit, remote sensing data for time points in the gap based on remote sensing data just before the gap and received local sensor data during the gap using a projection function, wherein the projection function is parametrized according to historical data sets of remote sensing data and local sensor data; providing, via the communication interface, projected remote sensing data at the identified point in time, where no remote sensing data exists.

In one implementation, a computer program or computer readable non-volatile storage medium comprising computer readable instructions is provided, which when loaded and executed by a processing device perform the methods, as described herein.

The provided method and system for example has the following relevance for practical farming. In regard of field zone specific relevance, using the ground truth, in-situ measurements to calibrate zoning algorithm by fusing satellite data and in-situ hyperspectral measurements results in more accurate and consistent data for zoning. In regard of continuous monitoring relevance, using spectral information from local sensor in conjunction with satellite data allows continuous, spatially explicit monitoring of plant health and growth at the field zone level.

The provided method and system for example has the following benefits for farm operations and farm labor. Improved logistics is provided due to the everyday availability of variable rate prescription maps for e.g. fungicide treatments growers do not need to plan their logistics around satellite image availability. Improved flexibility is provided. Non-stationary local sensors are highly movable, easy to install devices. Depending on seasonal progress local sensor can be installed on different fields, e.g. for T1, T2 or T3 cereal fungicide application. Improved efficiency is provided. Seamless, 1-click solution interoperability saves time, reduces installation stress factor and onboarding efforts. Improved maintenance is provided: Hundreds installed units confirm, the non-stationary local sensor and the system requires no maintenance.

The provided method and system for example has the following benefits for environment and energy. The non-stationary local sensor may use solar power, instead of batteries. More effective spraying helps farmers to act eco-friendly by reducing crop input and optimizing operations.

The provided method and system for example has the following impact on labor efficiency and/or labor safety. When well positioned in the field, farmers can reduce the efforts to visit fields and we can trigger much better targeted field visits, if needed at all.

FIGURES

Exemplary embodiments are shown in the drawings with

Figure 2:
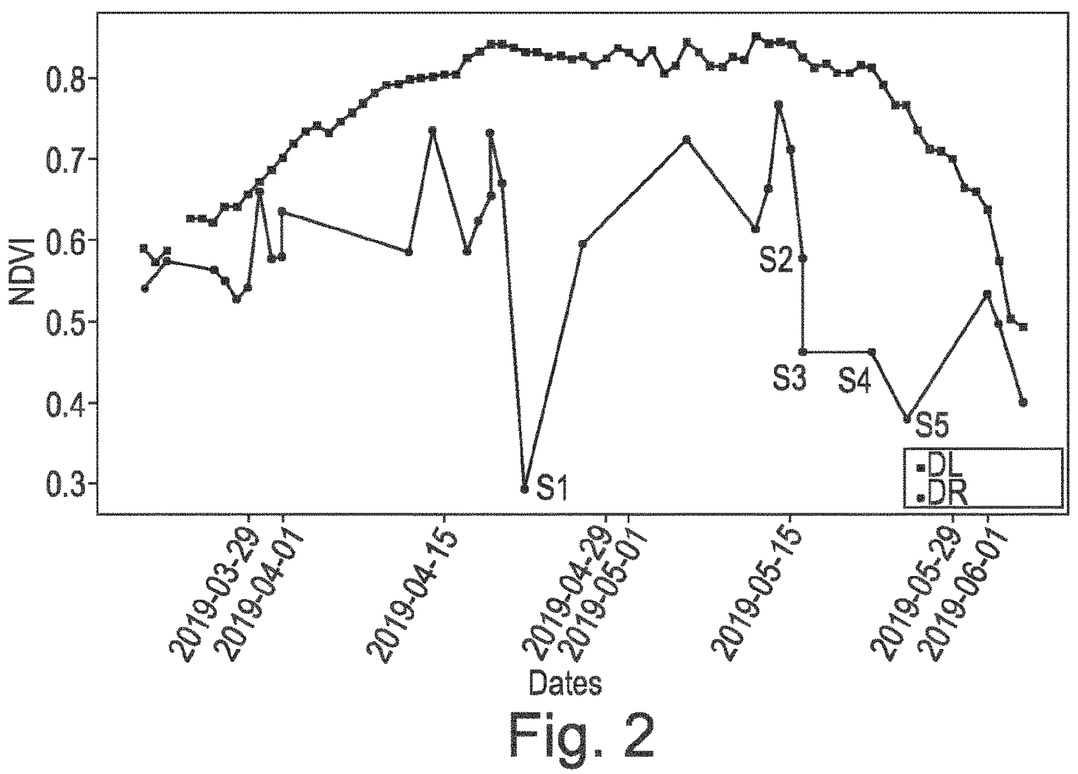
Figure 3:
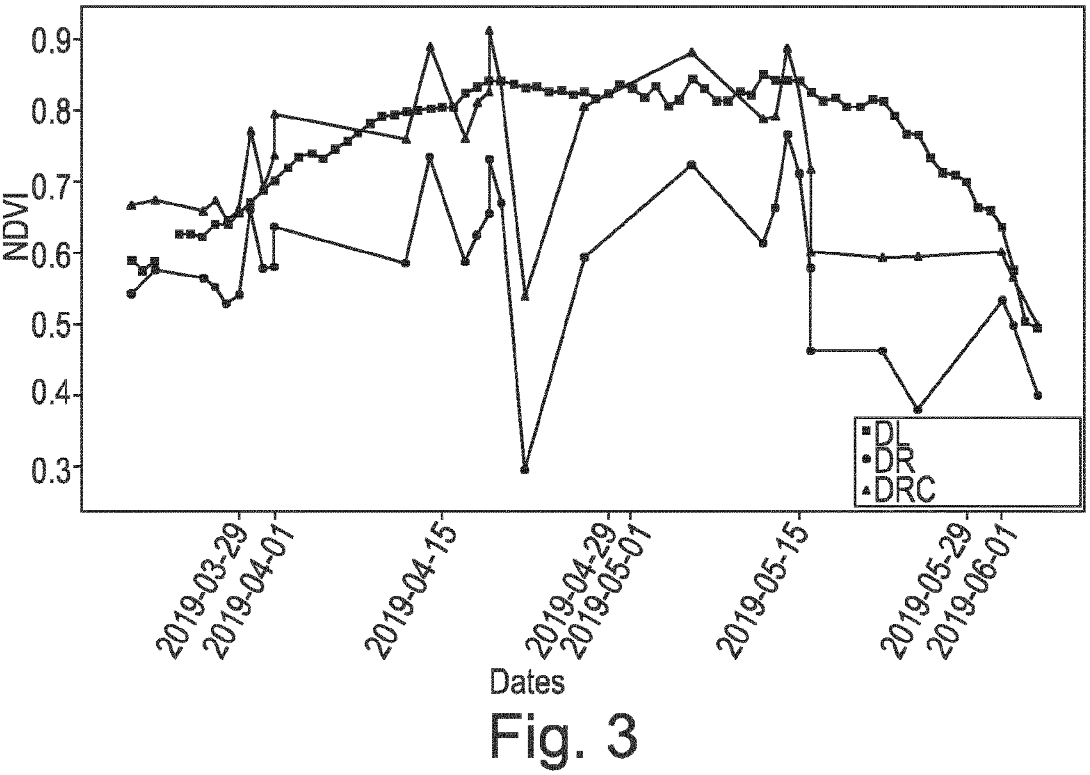
Figure 4:
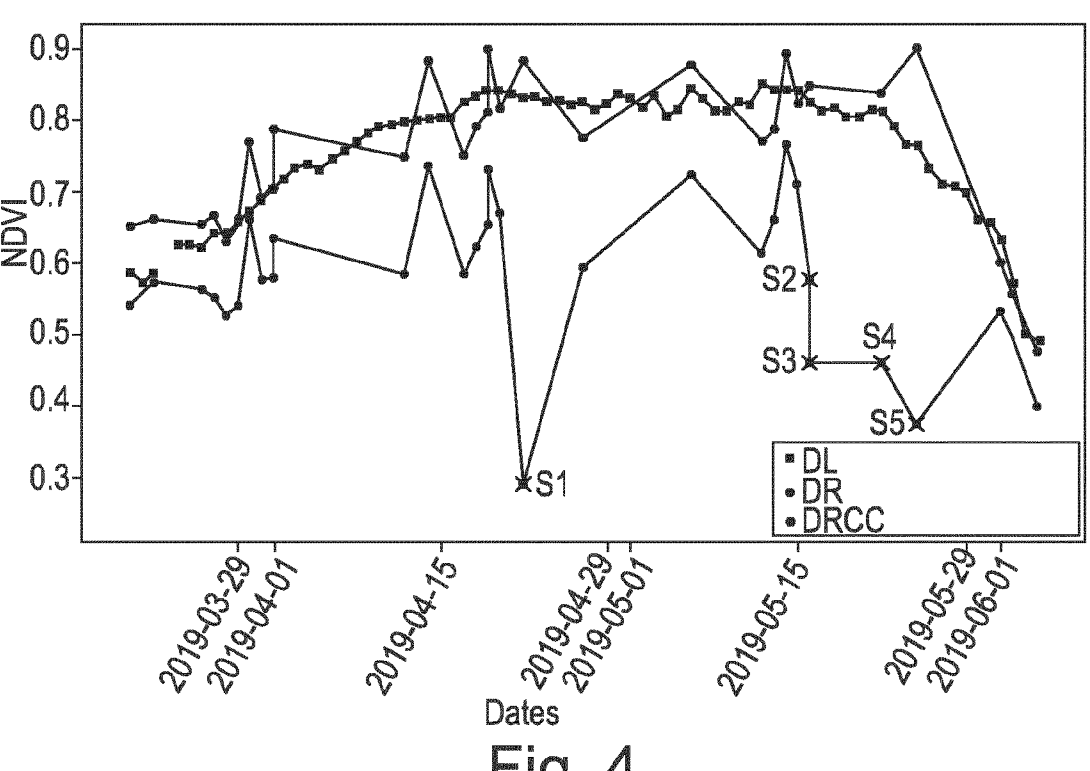
Figure 5:
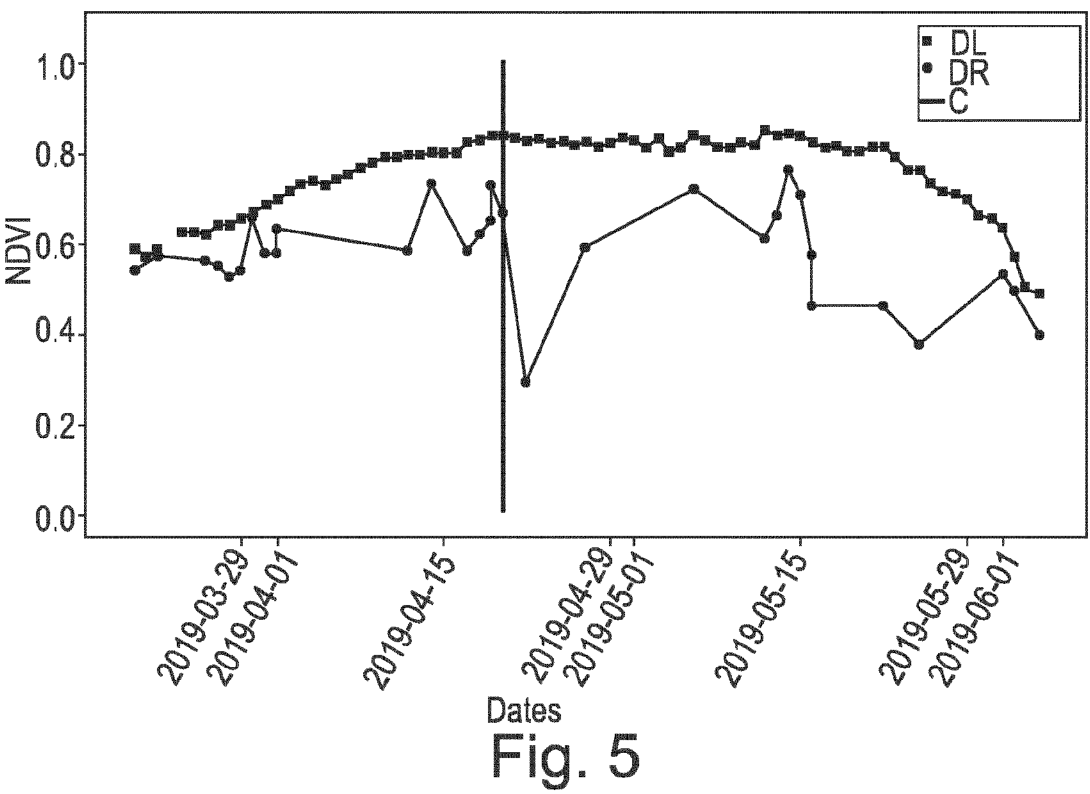
Figure 6:
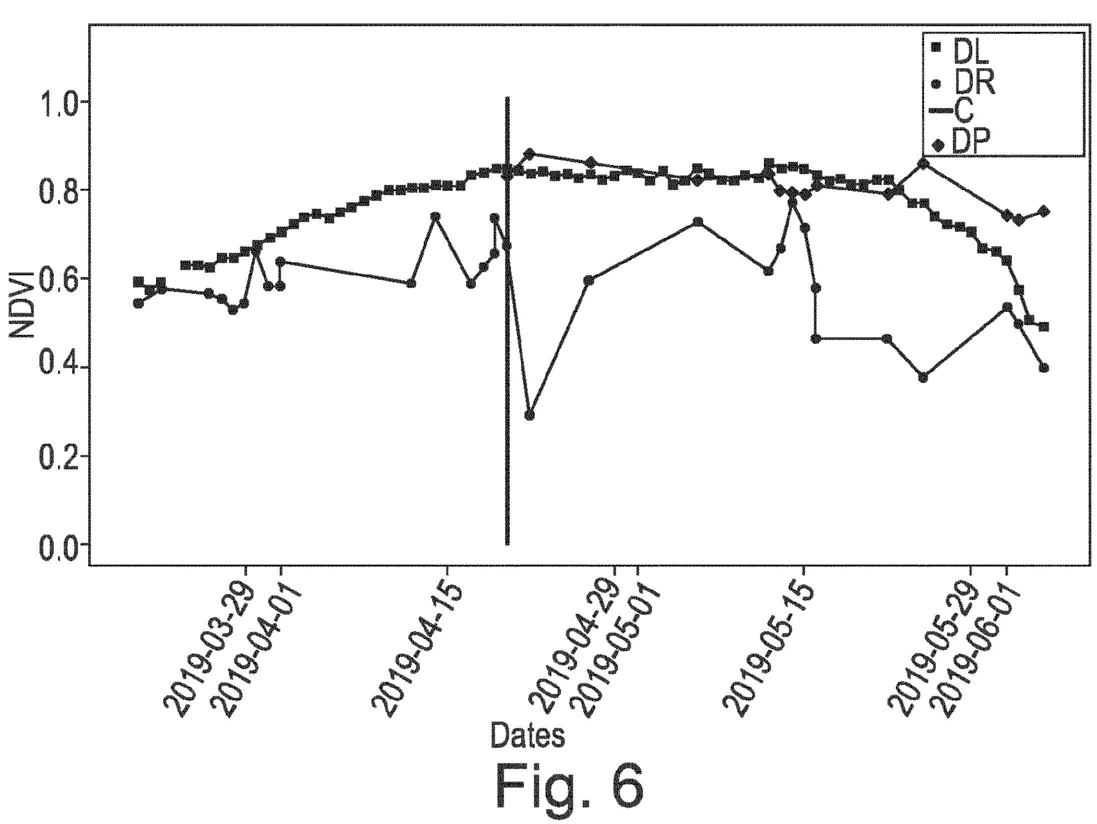
Figure 7A:
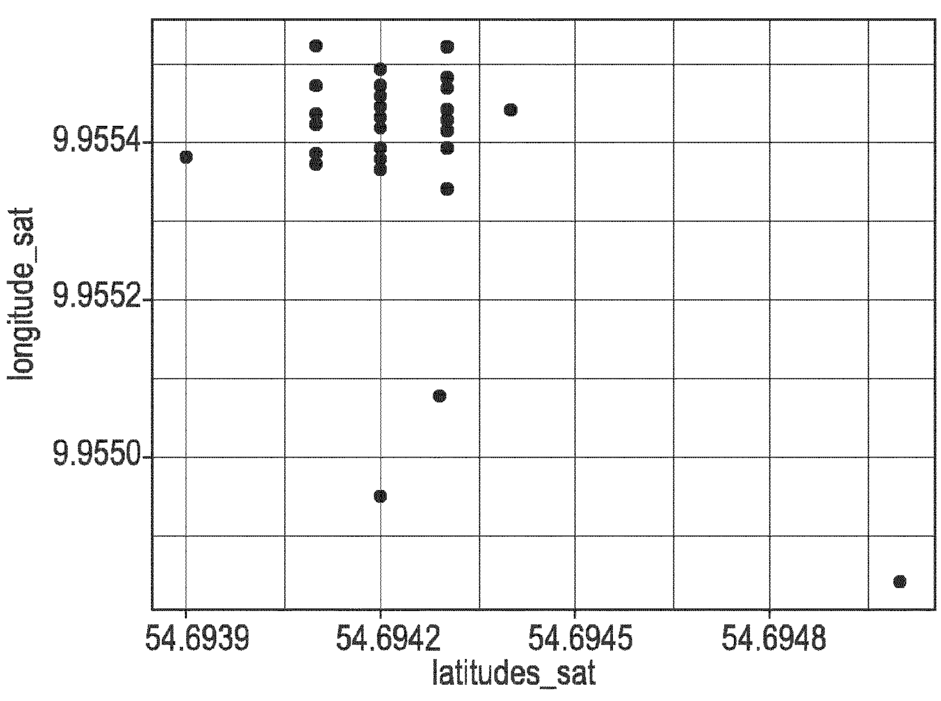
Figure 7B:
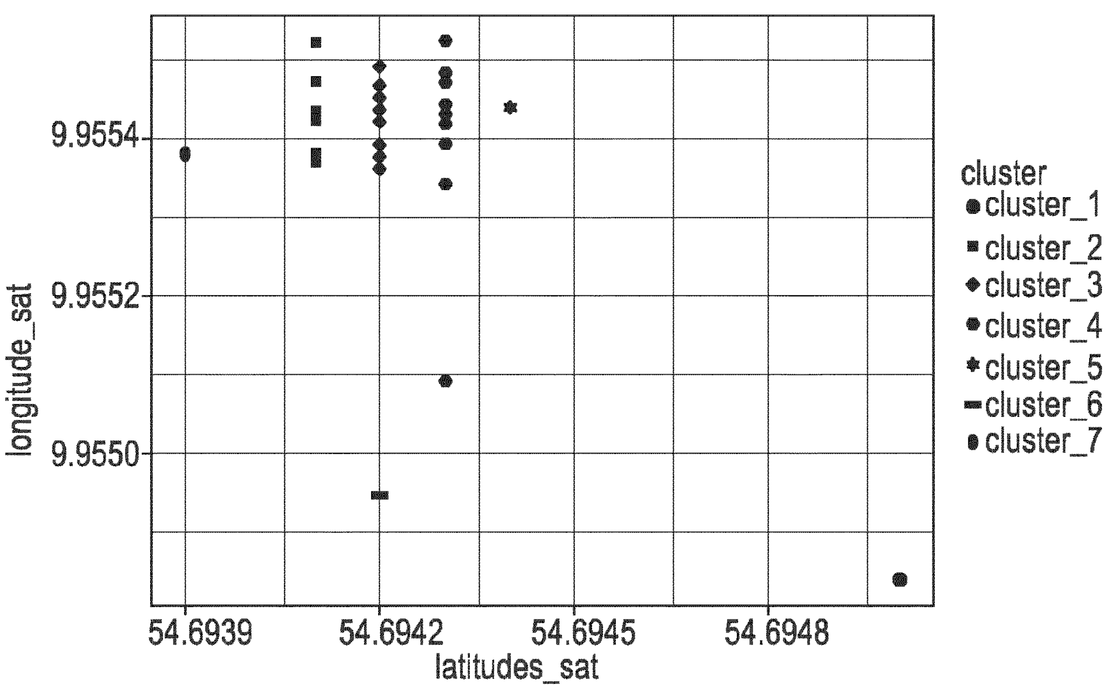
Figure 8:
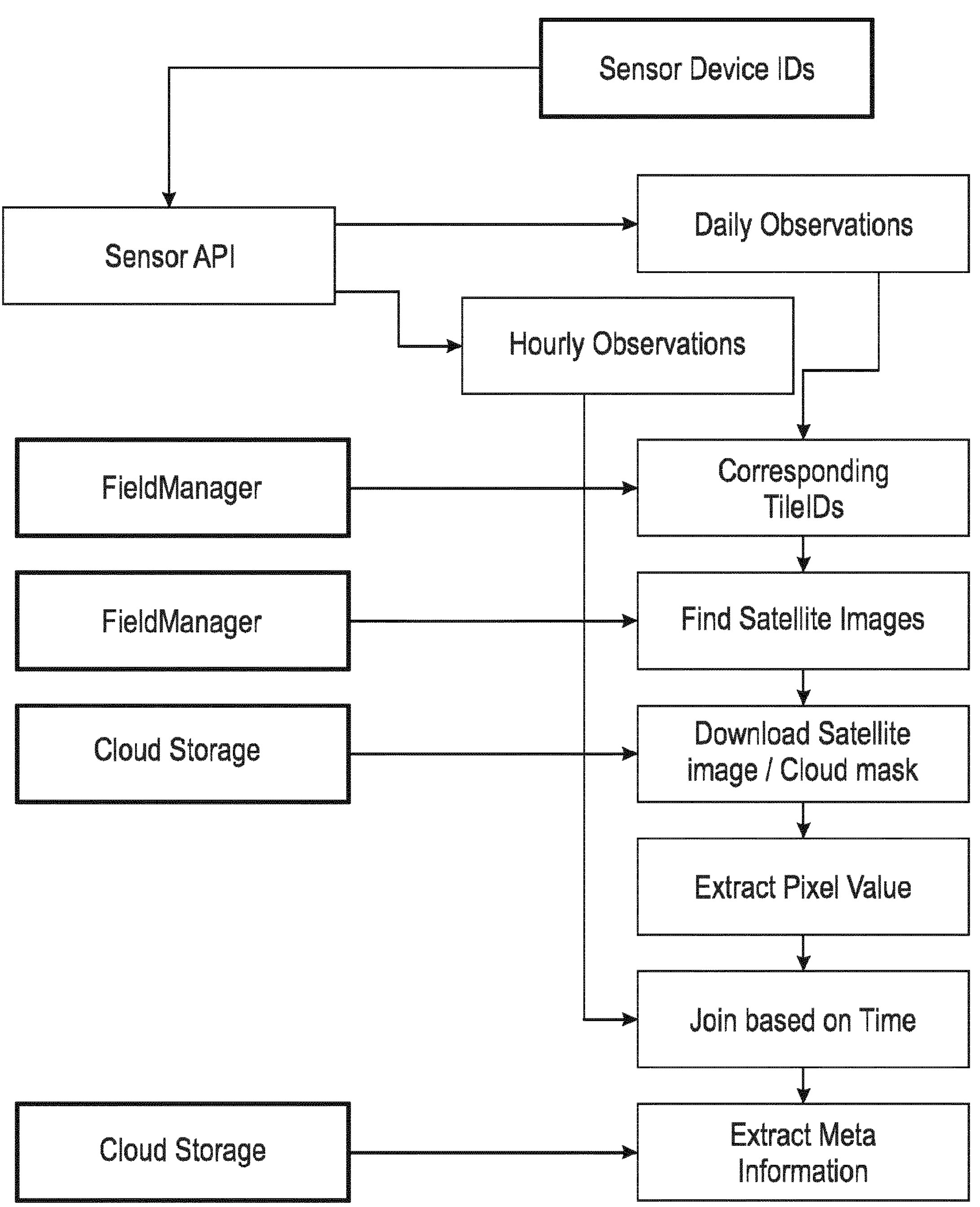

FIG. 1 depicting an exemplary embodiment of NDVI vs time from remote sensor data and local sensor data;

FIG. 2 depicting an exemplary embodiment of another NDVI vs time from remote sensor data and local sensor data;

FIG. 3 depicting an exemplary embodiment of predicted satellite measurements;

FIG. 4 depicting an exemplary embodiment of predicted satellite measurements with rejections;

FIG. 5 depicting an exemplary embodiment of another NDVI vs time from remote sensor data and local sensor data with a cut off;

FIG. 6 depicting an exemplary embodiment of NDVI vs time from remote sensor data and local sensor data with a prediction from the cut off;

FIG. 7A depicting an exemplary embodiment of location data from non-stationary local sensor;

FIG. 7B depicting an exemplary embodiment of clustered location data from non-stationary local sensor; and FIG. 8 depicting an exemplary embodiment of a flow chart for sensor fusion.

EMBODIMENTS OF THE INVENTION

FIG. 1 depicts an exemplary embodiment of a normalized difference vegetation index, NDVI, over time, in form of different dates, from remote sensor data DR, in particular satellite measurements, and local sensor data DL and highlights the differences particularly for a first image 1, a second image 2, a third image 3, a fourth image 4 and a fifth image 5 strongly diverging from local sensor data, which is a sign of atmospheric distortions such as clouds.

FIG. 2 depicts an exemplary embodiment of another NDVI over time from remote sensor data DR and local sensor data DL. In view of the NDVI of each image, the remote sensor data DR in particular deviate from the local sensor data DL in a first data point S1, a second data point S2, a third data point S3, a fourth data point D4 and a fifth data point S5. This again is a sign of atmospheric distortion such as clouds.

FIG. 3 depicts an exemplary embodiment of the remote sensor data DR and the local sensor data DL of FIG. 2. In general, the remote sensor data DR have a lower NDVI as the local sensor data DL, as the remote sensor data DR usually are determined by a satellite and distortions like atmospheric distortions have a higher impact on the remote sensor data DR than on the local sensor data DL. Consequently, the remote sensor data DR introduce a systemic underestimation of the real condition. This systemic underestimation difference in NDVI is overcome by correcting the remote sensor data, in this case current remote sensor data, to corrected current remote sensor data DRC based on the local sensor data DL and the remote sensor data DR. According to an embodiment, a correction model or prediction model, in particular a machine learning model, determines the corrected remote sensor data DRC. In other words, the systemic underestimation difference of the local sensor data DL and the remote sensor data DR is determined and added to the remote sensor data DR to determine the corrected remote sensor data DRC. In other words, the values of the remote sensor data DR are increased by the determined systemic underestimation difference in NDVI. In this case, it is determined that in average over the analyzed time, the local sensor data DL have an NDVI that is 0.1 higher than the remote sensor data DR. Consequently, each data point of the remote sensor data DR is increased by 0.1 to arrive at the corrected remote sensor data DRC. In the graph, the remote sensor data DR are shifted up by 0.1. The systemic underestimation difference can alternatively be a predetermined value, for example from former test cycles. Thus, the corrected remote sensor data DRC indicate a corrected version of the remote sensor data DR.

FIG. 4 depicts an exemplary embodiment of the remote sensor data DR and the local sensor data DL of FIG. 3. In addition to only determining reasonable corrected remote sensor data DPC, the correction model is configured for detecting outliers in the remote sensor data DR. As described in FIG. 3, a first data point S1, a second data point S2, a third data point S3, a fourth data point D4 and a fifth data point S5 deviate heavily from the corresponding local sensor data DL. The correction model compares the measurement values or in other words the NDVI values, of the remote sensor data DR and the local sensor data DL in each point in time and determines outliers if the difference of the remote sensor data DR and the local sensor data DL exceed a threshold. This threshold can be predetermined. Alternatively, the threshold can be dynamically adjusted by the correction model. Consequently, the determined outliers are not considered anymore, as they most likely correspond to unreasonable images. Thus, the correction model determines corrected remote sensor data with corrections DRCC, wherein the outliers of the remote sensor data DR are replaced by the correction model by corrected data points based on the corrected remote sensor data DRC and the local sensor data DL. Alternatively, instead of the rejected image that caused the outlier NDVI data, the correction model takes the NDVI of the last non-rejected image from the satellite to determine the corrected remote sensor data with corrections DRCC.

FIGS. 5 and 6 depict an exemplary embodiment of further local sensor data DL and remote sensor data DR over time. In this case, it is assumed that after a cut off C, no more satellite images, and thus no more remote sensor data DR are available. Thus, the correction model predicts predicted sensor data DP based on the local sensor data DL after the cut off as well as the local sensor data DL and the remote sensor data DR before the cut off. Consequently, the correction model can fill out gaps for remote sensor data that are missing.

FIG. 7A shows an exemplary embodiment of location data from non-stationary local sensor. The measurement error in the locations of the sensor device are highlighted via the reported observations of the locations of the device that vary. Hence, the unique location of the sensor devices has to be found via e.g. single-linkage hierarchical clustering algorithm. In identified clusters points are merged with minimal distance and a stop is introduced at a specified maximal distance. FIG. 7B shows the clustered location data from non-stationary local sensor.

FIG. 8 shows an exemplary embodiment of a flow chart for sensor fusion. To find corresponding satellite data for the local sensor data hourly, daily data for all available times/dates are extracted, in particular via a sensor application programming interface, sensor API. Based on daily data corresponding sensor device IDs from remote sensor data, in particular satellite data, for each observation are identified. Given the sensor device IDs corresponding data is retrieved from a field manager to find satellite data, or in other words satellite images, matching the date of the observation.

The field manager comprises a field related database, in which the local sensor data is stored, as well as a decision support system for finding the relevant satellite data. Alternatively, the local data is stored in a cloud storage. Then a download of the surrounding pixels of the image for the location of the local sensor device is conducted. The download is conducted from a cloud storage, in which the satellite data is stored. The cropped satellite images for visual analysis may be stored and correct pixel values in relation to the local sensor data are identified. Based on the time of the satellite image and the local observations are joined. Lastly meta information of the satellite image (i.e. angle of the satellite) may be extracted.

In one embodiment, the methods disclosed herein provide field zone management solution combining in-field local sensor data from e.g. non-stationary local sensor, with satellite-based biomass and crop health indices. Using local sensor data, leads to more accurate zone spray and allows for increased biomass, crop health maps and variable rate prescription map availability.

Crop optimization platforms may include all the way from data collection and generation, through agronomic modelling, deriving insights to recommending action. With such platforms a grower knows when, where and how much to apply (e.g. fungicides). Certain further functionalities may include on in field variability in application or spray maps, and further instructions on e.g. the tank mix and the optimal treatment window for variable rate application. This may be particularly useful for fungicides. Monitoring functionalities may enable growers to inspect and compare plant growth and health across time and fields—daily and from every on the planet using our web and mobile solutions.

Local sensors (e.g. non-stationary) may by smart in the sense of having multiple sensor elements, highly-moveable, easy-to-install IoT devices with sensor elements such as spectrometers or acoustic distrometers that is solar powered. Due to their design and manufacturing they may be virtually maintenance free.

By combining crop optimization platform with an in-field local sensor (e.g. non-stationary) the full automation and scalability potential of such platform yet backing up precise biomass, crop health analytic maps and variable rate application maps with the ground truth data may be exploited.

Trials support that this reduces biases e.g. in satellite-derived biomass and crop health indices. Additionally, through smartly combing satellite with local sensor data issues in satellite image availability can be overcome.

To keep the onboarding of the local sensor (e.g. non-stationary) into a platform simple, seamless 1-click solution may be included in the platform. This provides convenience of having a one-stop-shop solution for inspecting how crops grow and taking actions based on the platform supported by in-field data from the local sensor.

The invention claimed is:

1. A computer-implemented method for correcting remote sensor data of one or more agricultural fields, the method comprising:

sensing remote sensor data for a first agricultural field using a remote sensor, the remote sensor data comprising at least one remote measurement value corresponding to a location of the first agricultural field at a point in time, wherein the remote measurement value is associated with a hyperspectral index or a biomass index;

receiving local sensor data for the first agricultural field from at least one local sensor, the local sensor data comprising at least one local measurement value corresponding to a location of the local sensor and a point in time correlating to the location and point in time of the remote measurement value;

determining a correction model based on the previously received local sensor data and the previously received remote sensor data;

applying the correction model to current remote sensor data to generate corrected current remote sensor data.

2. The method of claim 1, wherein the local sensor is non-stationary.

3. The method of claim 1, wherein the local measurement value is associated with a hyperspectral index or a biomass index.

4. The method of claim 1, further comprising the steps after having received the remote sensor data and the local sensor data:

determining the remote measurement value corresponding to the location of the at least one local sensor; and determining a difference between the remote measurement value corresponding to the location of the at least one local sensor and the local measurement value of the at least one local sensor for a plurality of points in time, wherein determining the correction model is further based on the determined difference.

5. The method of claim 4, wherein determining the difference between the remote measurement value corresponding to the location of the at least one local sensor and the local measurement value of the at least one local sensor for a plurality of points in time comprises the steps:

receiving local time series data of the local sensor data (DL) from the at least one local sensor, wherein the local time series data comprises a plurality of location data of a plurality of points in time corresponding to the location, where the at least one local sensor is located at a specific point in time;

determining a cluster of local sensor data based on a maximal distance between the respective locations of the local sensors over time;

determining a clustered location of the at least one local sensor based on the determined cluster; and determining the difference between the remote measurement value corresponding to the clustered location of the at least one local sensor and the local measurement value of the at least one local sensor for a plurality of points in time, wherein determining the correction model is further based on the determined difference.

6. The method of claim 5, wherein the clustered location is determined by determining a center of the cluster.

7. The method of claim 1, wherein the remote sensor data comprises at least one remote image, which is based on the at least one remote measurement value;

wherein determining the remote measurement value corresponding to the location of the local sensor comprises the step:

extracting a pixel from the remote image that is closest to the location of the local sensor or extracting a mean of pixels within a predefined distance of the pixel closest to the location of the local sensor; and determining the remote measurement value based on the extracted pixel, wherein determining the correction model is also based on the extracted pixel on which the remote measurement value bases.

8. The method of claim 1, wherein the method comprises the steps:

if received remote time series data associated with the remote sensor data (DR) comprises at least one gap, where the remote sensor data (DR) at an expected point in time in the time series of remote time series data (DR) are missing; then receiving local sensor data (DL) for the point in time of the gap; and determining predicted remote sensor data (DP) for a point in time of the gap based on the received local sensor data (DL).

9. The method of claim 8, wherein determining the predicted remote sensor data (DP) comprises:

receiving remote sensor data (DR) of a point in time just before the gap; and determining the predicted remote sensor data (DP) based on the received remote sensor data (DR) of the point in time just before the gap.

10. The method of claim 1, wherein the correction model comprises a projection function depending on historical data sets of remote sensor data and local sensor data, and wherein the remote sensor data is determined based on the projection function.

11. A non-transitory computer readable storage medium having instructions encoded thereon that, when executed by a processing device, cause the processing device to perform the method of claim 1.

12. The method of claim 1, wherein the remote sensor data (DR) and the local sensor data (DL) are used for monitoring the agricultural field.

13. A processing device, configured to: sense remote sensor data for a first agricultural field by using a remote sensor, wherein the remote sensor data is received and comprises at least one remote measurement value corresponding to at least one location that is measured by the remote sensor at at least one point in time of obtaining the remote measurement value, corresponding to a location of the first agricultural field at a point in time, wherein the remote measurement value is associated with a hyperspectral index or a biomass index;

receive local sensor data for the first agricultural field from at least one local sensor, wherein the local sensor data comprises at least one local measurement value corresponding to at least one location of the at least one local sensor and corresponding to at least one point in time of obtaining the local measurement value correlating to the location and point of time of obtaining the remote measurement value, wherein the local measurement value corresponds to a location of the local sensor and a point in time correlating to the location and point in time of the remote measurement value;

determine a correction model based on the previously received local sensor data and the previously received remote sensor data;

apply the correction model to current remote sensor data to generate corrected current remote sensor data.

14. A system for correcting remote sensor data of one or more agricultural fields, comprising:

a remote sensor, configured for providing remote sensor data for the first agricultural field from a remote sensor, wherein the remote sensor data comprises at least one remote measurement value corresponding to at least one location that is measured by the remote sensor at at least one point in time of obtaining the remote measurement value, corresponding to a location of the first agricultural field at a point in time, wherein the remote measurement value is associated with a hyperspectral index or a biomass index;

a local sensor, configured for providing local sensor data for the first agricultural field from at least one local sensor, wherein the local sensor data comprises at least one local measurement value corresponding to at least one location of the at least one local sensor and corresponding to at least one point in time of obtaining the local measurement value correlating to the location and point of time of obtaining the remote measurement value, wherein the local measurement value corresponds to a location of the local sensor and a point in time correlating to the location and point in time of the remote measurement value; and the processing device of claim 13.

15. A method for correcting remote sensor data of one or more agricultural fields, the method comprising:

sensing, by a remote sensor, remote sensor data including at least one remote measurement value corresponding to at least one location that is measured by the remote sensor at at least one point in time of obtaining the remote measurement value, for a first agricultural field using the remote sensor, the remote sensor data comprising at least one remote measurement value corresponding to a location of the first agricultural field at a point in time, wherein the remote measurement value is associated with a hyperspectral index or a biomass index;

receiving local sensor data for the first agricultural field from at least one local sensor, wherein the local sensor data comprises at least one local measurement value corresponding to at least one location of the at least one local sensor and corresponding to at least one point in time of obtaining the local measurement value correlating to the location and point of time of obtaining the remote measurement value, wherein the local measurement value corresponds to a location of the local sensor and a point in time correlating to the location and point in time of the remote measurement value;

determining a correction model based on the previously received local sensor data and the previously received remote sensor data;

applying the correction model to current remote sensor data to generate corrected current remote sensor data.

* * * * *